(12) United States Patent
Bloemer

(10) Patent No.: US 8,818,516 B2
(45) Date of Patent: Aug. 26, 2014

(54) POSTURE-DEPENDENT STIMULATION FOR IMPLANTABLE STIMULATORS

(75) Inventor: Frank Bloemer, Berlin (DE)

(73) Assignee: Biotronik SE & Co. KG (DE)

( * ) Notice: Subject to any disclaimer, the term of this patent is extended or adjusted under 35 U.S.C. 154(b) by 0 days.

(21) Appl. No.: 13/372,652

(22) Filed: Feb. 14, 2012

(65) Prior Publication Data

US 2012/0232614 A1    Sep. 13, 2012

Related U.S. Application Data

(60) Provisional application No. 61/451,128, filed on Mar. 10, 2011.

(51) Int. Cl.
| A61N 1/00 | (2006.01) |
| A61N 1/36 | (2006.01) |
| A61N 1/365 | (2006.01) |

(52) U.S. Cl.
CPC ......... *A61N 1/36128* (2013.01); *A61N 1/36535* (2013.01); *A61N 1/36521* (2013.01)
USPC .......................................................... 607/46

(58) Field of Classification Search
CPC ............................. A61N 1/36; A61N 1/36021
USPC ....................................................... 607/46, 2
See application file for complete search history.

(56) References Cited

U.S. PATENT DOCUMENTS

| 5,031,618 A | 7/1991 | Mullett |
| 6,044,297 A | 3/2000 | Sheldon et al. |
| 7,257,447 B2 * | 8/2007 | Cates et al. ..................... 607/59 |
| 7,313,440 B2 | 12/2007 | Miesel |
| 2005/0245988 A1 * | 11/2005 | Miesel ............................. 607/46 |
| 2006/0167513 A1 | 7/2006 | Rouw et al. |
| 2007/0115277 A1 | 5/2007 | Wang et al. |
| 2008/0164979 A1 | 7/2008 | Otto |
| 2009/0076336 A1 | 3/2009 | Mazar et al. |
| 2010/0010381 A1 | 1/2010 | Skelton et al. |
| 2010/0211135 A1 | 8/2010 | Caparso et al. |
| 2010/0298899 A1 | 11/2010 | Donnelly et al. |

OTHER PUBLICATIONS

European Search Report, Appln. No. 12157036.0-2305, May 10, 2012.

* cited by examiner

*Primary Examiner* — Christopher D Koharski
*Assistant Examiner* — Nadia Ahmad
(74) *Attorney, Agent, or Firm* — Craig A. Fieschko, Esq.; DeWitt Ross & Stevens S.C.

(57) ABSTRACT

A therapeutic stimulator, e.g., a spinal neurostimulator for pain relief, adapts stimulation delivered to the patient in dependence on measurements of patient orientation (e.g., from a three-axis accelerometer), and also on impedance measurements from leads situated within or upon the patient's body (e.g., from electrodes on neurostimulation leads extending alongside the spine). Since the impedance measurements can provide additional data regarding body positioning, as well as providing data regarding electrode status (such as lead migration, electrode encapsulation, etc.), use of the impedance measurements can provide more refined (and more appropriate) control of delivered stimulation.

23 Claims, 2 Drawing Sheets

POSTURE-DEPENDENT STIMULATION FOR IMPLANTABLE STIMULATORS

CROSS-REFERENCE TO RELATED APPLICATIONS

This application claims priority under 35 USC §119(e) to U.S. Provisional Patent Application 61/451,128 filed Mar. 10, 2011, the entirety of which is incorporated by reference herein.

FIELD OF THE INVENTION

This document concerns an invention relating generally to implantable stimulators, and more specifically to adjustment of neurostimulation parameters in dependence on changes in patient body positioning.

BACKGROUND OF THE INVENTION

As discussed in (for example) U.S. Pat. No. 5,031,618 to Mullett, U.S. Pat. No. 7,313,440 to Miesel, and U.S. Patent Appln. Pub. 2010/00010381 to Skelton et al., implantable stimulators are sometimes used to deliver electrical stimulation to the spinal cord (or other tissue) of a patient via one or more implantable leads, typically to alleviate pain or provide other therapeutic effects. An exemplary arrangement of this nature is depicted in the accompanying FIG. 1, wherein an implantable stimulator 100 is shown implanted within a patient's body with a pair of leads 102 extending from the stimulator adjacent the spinal column. The leads bear electrodes (not shown) spaced along their surfaces through which stimulation is delivered to the spinal cord. The delivered stimulation can generate a tingling sensation that tends to mask, or sometimes entirely eliminate, the patient's pain.

As the foregoing references note, it can be desirable to vary stimulation parameters (e.g., pulse amplitude, pulse width, and/or pulse frequency) depending on the patient's body orientation; for example, a patient using an implantable spinal neurostimulator for chronic pain relief may require less stimulation when standing up than when the patient is recumbent. An input device 104 can be used by the patient, or by medical personnel, to adjust the stimulation parameters. Alternatively or additionally, a stimulator may incorporate an accelerometer or other orientation sensor which automatically adjusts stimulation based on the orientation of the sensor (which tends to indicate the patient's posture), and possibly based on motion of the sensor as well, e.g., how long the patient remains in a particular orientation.

While automatic adjustment of stimulation based on patient orientation and activity is useful, it can sometimes fail to adequately adjust stimulation. For example, such stimulation adjustment techniques may provide the same stimulation when a patient is standing and facing forwardly, and when the patient is seated upright but with his/her head, shoulders, and torso turned to look rearwardly. In this case the patient's detected orientation is the same, but his/her actual body positioning is very different, and certain patients may need different stimulation for such different body positions. It would therefore be useful to have further stimulation adjustment schemes which improve on conventional methods.

SUMMARY OF THE INVENTION

The invention, which is defined by the claims set forth at the end of this document, is directed to implantable stimulation devices and stimulation methods which at least partially alleviate the aforementioned problems. A basic understanding of some of the features of preferred versions of the invention can be attained from a review of the following brief summary of the invention, with more details being provided elsewhere in this document. To assist in the reader's understanding, the following review makes reference to the accompanying drawings (which are briefly reviewed in the "Brief Description of the Drawings" section following this Summary section of this document).

The accompanying FIG. 2 schematically illustrates an exemplary implantable stimulator 200, which includes a stimulation generator 206 configured to deliver electrical stimulation to one or more electrodes 208 of one or more electrode-bearing leads 202 (with two eight-electrode leads 202 being schematically shown). The stimulator 200 additionally includes an orientation sensor 210, e.g., a 3-axis accelerometer, which provides an orientation output signal indicative of the orientation of the orientation sensor 210 (and thus the orientation of the patient, or at least the orientation of that portion of the patient's body that bears the orientation sensor 210). Preferably, the orientation sensor 210 is capable of providing an orientation output signal which is indicative of whether the patient is standing or lying down, and whether the patient is lying prone (stomach and face down), supine (stomach and face up), or on his/her right or left side, as well as providing output signals indicating whether the patient is between some of these positions. A controller 212 then adjusts the electrical stimulation delivered by the stimulation generator 206 in dependence on the orientation output signal from the orientation sensor 210. For example, the controller 212 may apply a control algorithm that decreases stimulation as a patient moves from a standing position to a lying position.

However, unlike prior stimulation systems, the stimulator 200 additionally includes a lead impedance sensor 214 configured to determine the impedance(s) of the electrode(s) 208 of the electrode-bearing lead(s) 202, e.g., one or more bipolar impedances (impedances measured between electrodes 208) and/or one or more monopolar impedances (impedances measured between an electrode 208 and some other location, e.g., the housing 216 of the stimulator 200). Such impedances are indicative of the impedance (electrical resistance) of the body tissue between the locations from which impedance is measured. These impedances can change with body position owing to changes in blood flow, tissue density, etc., and therefore these impedances can also provide information regarding body position. The controller 212 is therefore preferably configured to adjust the electrical stimulation delivered by the stimulation generator 206 in dependence on the impedance(s) of the electrode(s) 208, as well as on the detected orientation at or about the time the impedance(s) were measured. The impedance and orientation data are believed to provide a more complete representation of patient body position than orientation data alone.

The orientation and impedance data is preferably stored and/or processed in the form of impedance vectors: data which encode the orientation output signal from the orientation sensor 210 and the impedance(s) of the electrode(s) 208. A memory 218 stores data which relates the impedance vectors to stimulation parameters which define the electrical stimulation delivered by the stimulation generator 206. Thus, when a patient has impedance vectors—orientation and electrode impedance(s)—which meet certain characteristics, the controller 212 adapts the stimulation generator 206 to deliver stimulation appropriate for the patient's current state. The stimulation parameters are preferably set via an input device 204 in wireless (or wired) communication with a transceiver 220 associated with the stimulator 200, as schematically depicted in FIG. 2. As the patient proceeds with his/her everyday activities, the patient (and/or a programmer, such as a doctor or other medical technician) can adjust stimulation parameters to a comfortable level, and the impedance vectors at the time of adjustment can be stored in relation to these input stimulation parameters. This process is schematically illustrated in FIG. 3, wherein impedance vectors reflecting the impedances of eight electrodes at five different body positions are shown, with stimulation parameters P1, P2, P3, etc. being assigned to each impedance vector. Initially, some set of baseline or default stimulation parameters might be applied across the range of possible impedance vectors. As the patient or programmer enters preferred stimulation parameters at particular impedance vectors, the default stimulation parameters might be overwritten at and/or adjacent to these vectors. As the matrix of impedance vectors and preferred stimulation parameters is populated, the controller 212 might interpolate or otherwise calculate new stimulation parameters to use in place of default stimulation parameters if new impedance vectors are encountered and no corresponding preferred stimulation parameters have yet been input. Thus, the relationship between stimulation parameters and impedance vectors might be stored in the nature of a "look-up table," wherein measured impedance vectors that do not correspond precisely to those stored in the table can be assigned the stimulation parameters of the closest stored impedance vectors, or can be assigned stimulation parameters via interpolation or other calculation. Alternatively (or additionally), the relationship between stimulation parameters and impedance vectors might be stored in the nature of equations or other algorithms which assign stimulation parameters to measured impedance vectors, whereby the electrical stimulation delivered by the stimulation generator 206 is automatically adapted to the patient's current state.

Further advantages, features, and objects of the invention will be apparent from the remainder of this document in conjunction with the associated drawings.

DETAILED DESCRIPTION OF PREFERRED VERSIONS OF THE INVENTION

Figure 1:
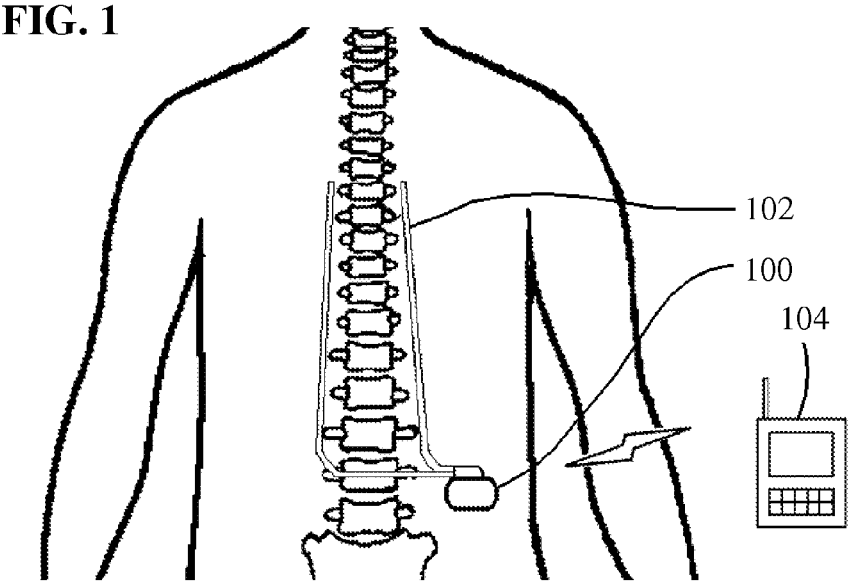
FIG. 1 is a schematic depiction of a conventional spinal neurostimulation unit 100 with a pair of electrode-bearing leads 102 situated adjacent a patient's spine to deliver pain-relieving electrostimulation, and an input device 104 usable by the patient (or by a programmer) to adjust stimulation, view data regarding stimulation settings, etc.

Expanding on the discussion above, the invention improves upon prior stimulation delivery systems which adjust stimulation in dependence on detected orientation and/or activity by adjusting stimulation in response to impedance data as well. In a spinal neurostimulator 200, orientation data typically only reflects whether the patient's torso is oriented vertically or horizontally (or at some inclination therebetween), as well as reflecting the general direction the torso is facing when it is not vertical. However, such orientation data may not fully reflect curvature of the spine, and/or rotation of the spine along its axis—factors which may influence a patient's pain level in addition to the patient's orientation. Thus, by varying stimulation in accordance with both orientation data and impedance vectors (tissue impedances) measured from locations along the spine, a patient can achieve more comfortable and effective neurostimulation. The stimulation parameters (e.g., pulse amplitude, pulse width, and/or pulse frequency) delivered by each electrode 208 for a particular set of impedance vectors, and a particular orientation, can be defined by a patient and/or programmer and stored for later use, and/or can be calculated by interpolation, algorithms (e.g., algorithms derived from regression analysis of comfortable parameters previously specified by the patient), or other techniques.

Beneficially, where the invention allows updating of stimulation parameters by the patient or by a programmer over time—e.g., where a patient can reset a stimulation parameter when engaged in a particular activity (which will often correspond to a particular set of orientations and impedance vectors)—the invention also compensates for factors such as lead/electrode migration, tissue encapsulation of electrodes, and other events that can affect stimulation efficacy.

Preferred versions of the invention involve fully-implanted stimulators and leads, and input devices which are remote from (i.e., separate and spaced from) the stimulators 200, and which communicate wirelessly with the stimulators 200. However, it should be understood that throughout this document, "implantable" or "implanted" should be regarded as encompassing partially, as well as entirely, implantable or implanted. Thus, a stimulator 200 and/or its leads 202 might only be partially implanted, and might have portions situated externally of a patient's body which communicate with an input device 204 via wired or other communications. For example, a stimulator 200 might include an implanted stimulation generator 206, impedance sensor 214, and leads 202, and some or all of the remaining components depicted in FIG. 2 might be outside the body, and might communicate with the stimulation generator 206 and the impedance sensor 214 via wired or wireless communications.

The orientation sensor 210 is preferably a three-axis accelerometer, but other orientation sensors 210 such as 1-axis or 2-axis accelerometers, magnetometers or other "digital compasses," angle-sensitive switches or potentiometers (e.g., devices working on principles similar to those of mercury switches), and/or gyroscope-type systems could be used instead. The orientation sensor 210 need not be situated within the housing 216 of the stimulator 200, and could (for example) be situated elsewhere within the body, or externally of the body, to communicate with the stimulator 200 via wired or wireless communications.

Figure 2:
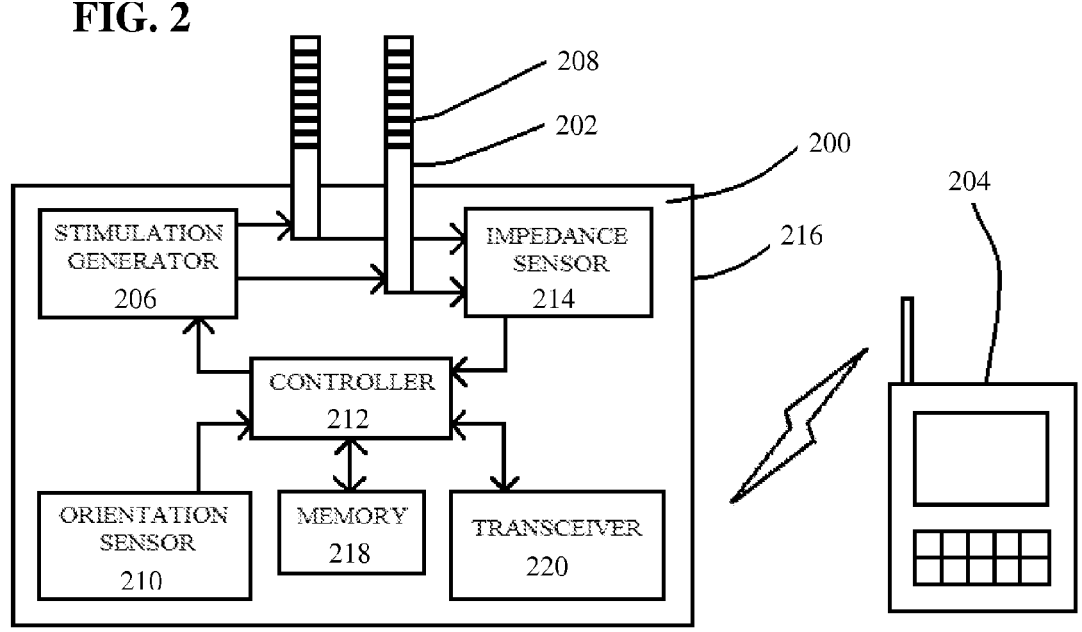
FIG. 2 is a simplified schematic depiction of an enhanced implantable stimulator 200 having an orientation sensor 210, and also including a lead impedance sensor 214 which determines the impedance of one or more of the electrodes 208 on one or more of the leads 202, wherein the stimulation generator 206 delivers electrical stimulation to one or more electrodes 208 in dependence on orientation data from the orientation sensor 210 and also from impedance data from the impedance sensor 214.

In practice, the leads 202 used with the stimulator 200 are typically provided separately from the stimulator 200, and are installed on the stimulator 200 during its implantation. While two multi-electrode leads 202 are depicted in FIG. 2, more or fewer leads 202 might be used, and each lead 202 may bear one or more electrodes 208. It should be understood that a single electrode 208 can be associated with multiple impedance values depending on whether monopolar impedance (e.g., between an electrode 208 and the stimulator housing 216) and/or bipolar impedance (e.g., between an electrode 208 and another electrode 208) is used.

Figure 3:
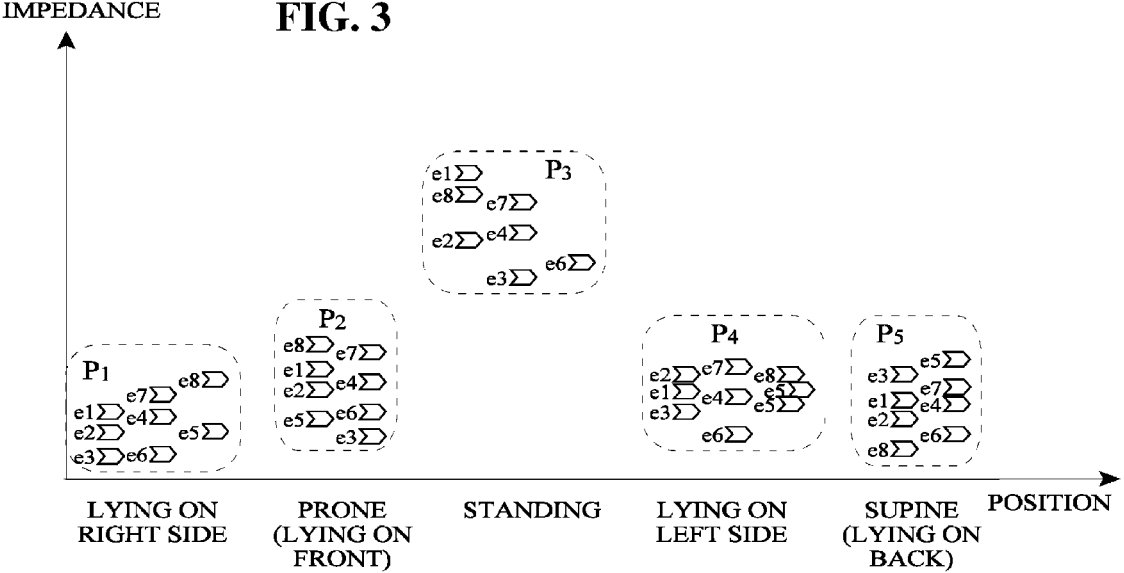
FIG. 3 is a schematic depiction of the collection of impedance vectors, i.e., sets of electrode impedance data (depicted as impedance readings e1, e2, ... e8) and patient orientation data, wherein stimulation parameters P1, P2, etc. (e.g., settings for stimulation pulse amplitude, pulse width, pulse frequency, etc.) are assigned to each impedance vector such that the patient will receive stimulation in accordance with P1, P2, etc. when the orientation sensor 210 and lead impedance sensor 214 detect impedance vectors similar or equal to the impedance vectors corresponding to P1, P2, etc.

It should be understood that the schematic depiction of impedance vectors and stimulation parameters shown in FIG. 3 is greatly simplified, and at each depicted patient orientation (as well as at patient orientations therebetween), there will often be a number of impedance vectors and stimulation parameters because the patient may have different body positioning (and thus different impedance measurements) at each orientation. Impedance vectors can be envisioned as a multi-dimensional matrix with one dimension corresponding to orientation data (or multiple dimensions corresponding to orientation data, if the orientation data is separated into orientation along separate axes), and with additional dimensions corresponding to impedance measurements from each electrode used to define patient stimulation. Stimulation parameters can be defined at each location or region within this multidimensional matrix such that when measured impedance vectors are at or near a particular location or region in the matrix, the corresponding stimulation parameters are applied. Since leads 202 for spinal neurostimulation typically bear eight or more electrodes 208 (and thus eight possible impedances, or more if bipolar impedances are used), the matrix of impedance vectors and stimulation parameters may have many dimensions. For simplicity, impedance vectors need not use impedances from all electrodes 208; for example, suitable adaptation of patient stimulation might be applied if the invention only applies stimulation parameters in dependence on impedances from every other electrode 208 on a lead 202, or from every third electrode 208, or simply from the most distal electrode 208, the most proximal electrode 208, and some electrode 208 at or near the midpoint therebetween. However, it is preferred that more impedance values from more electrodes 208 be used, since this may yield more information regarding the patient's body positioning. Thus, impedance vectors might include monopolar impedances from several or all electrodes 208 in FIG. 2 as well as (or instead of) bipolar impedances measured between electrodes 208 on the same lead 202, and/or bipolar impedances measured between electrodes 208 on different leads 202.

The invention might be used with more than one input device 204, for example, a patient input device having limited functionality (such as the ability to only adjust stimulation parameters in the form of pulse amplitude), and a doctor input device having greater ability to reprogram the stimulator 200 (such as the ability to assign one or more of pulse amplitude, pulse width, and/or pulse frequency stimulation parameters to be delivered upon measurement of a given impedance vector). Input devices can have different configurations and modes of communication with the stimulator 200; for example, a patient input device may be in the form of a tablet-type computer that wirelessly communicates with the stimulator 200 when situated nearby, and a doctor input device might be the doctor's desktop computer which communicates with the patient input device via the internet, with the patient input device serving to relay communications between the doctor input device and the stimulator 200.

An input device 204 is preferably also able to display data relating to measured impedance vectors and/or their corresponding stimulation parameters, e.g., correlations between impedance measurements and/or body orientations; stimulation parameters corresponding to particular impedance measurements and/or body orientations (perhaps accompanied by a graphical display of the body position indicated by the impedance measurements and/or body orientations); and similar data. Stimulation parameters defined by the patient need not be input in the form of stimulation settings per se, e.g., in the form of pulse amplitude, pulse width, pulse frequency, etc.; rather, they might be input as (for example) "pain ratings," e.g., patient pain as subjectively defined on a scale from 1-10, with each rating having an assigned stimulation setting (e.g., pulse amplitude, pulse width, and/or pulse frequency). It can be helpful to provide the patient with a display of impedance vectors versus such pain ratings, particularly if the impedance vectors are presented as graphical or other simplified depictions of body positioning. A patient might then more rapidly understand which body positions give rise to greater pain, and the patient might then adjust his/her behavior as desired.

Where a patient is allowed to define stimulation parameters—for example, pain ratings or other inputs relating to stimulation effectiveness—these need not be immediately implemented by the invention. Rather, patient-input stimulation parameters may first be reviewed by a doctor or other programmer, and/or by filters or algorithms, which then adjust the stimulation parameters to be applied going forward.

The invention might be used with additional or different forms of stimulation output, e.g., the stimulator 200 might contain or control a drug delivery device which delivers a drug to the patient in dependence on measured impedance vectors. Measured impedance vectors may also trigger alerts delivered to the input device 204, e.g., alerts related to lead failure or abnormal measurements.

While the invention is primarily intended for spinal neurostimulation applications, it might be used for other types of therapeutic stimulation as well, e.g., that of U.S. Pat. No. 6,044,297 to Sheldon et al. and/or U.S. Patent Appln. Pub. 2007/0115277 to Wang et al. The invention can also or alternatively incorporate components, techniques, and other features noted in the patents and other documents noted elsewhere in this document (and in the patents and documents cited in, and citing to, the noted patent and other references).

It should be understood that the versions of the invention described above are merely exemplary, and the invention is not intended to be limited to these versions. Rather, the scope of rights to the invention is limited only by the claims set out below, and the invention encompasses all different versions that fall literally or equivalently within the scope of these claims.

What is claimed is:

1. An implantable stimulator including:
   a. a stimulation generator configured to deliver electrical stimulation to an electrode of an electrode-bearing lead;
   b. a lead impedance sensor configured to determine the impedance of the electrode of the electrode-bearing lead;
   c. an orientation sensor configured to provide an orientation output signal indicative of the orientation of the orientation sensor;
   d. a controller configured to adjust the electrical stimulation delivered by the stimulation generator in dependence on:
      (1) the orientation output signal from the orientation sensor, and
      (2) the impedance of the electrode, wherein the impedance is within a normal operating impedance range representative of lack of faulty operation of the electrode-bearing lead.

2. The implantable stimulator of claim 1 further including a memory storing impedance vectors, each impedance vector encoding:
   a. the orientation output signal from the orientation sensor, and
   b. the impedance of the electrode,
   obtained at least substantially at the same time.

3. The implantable stimulator of claim 2 wherein each impedance vector encodes the impedances of two or more electrodes from an electrode-bearing lead.

4. The implantable stimulator of claim 2 wherein each impedance vector encodes the impedances from electrodes on two or more electrode-bearing leads.

5. The implantable stimulator of claim 2 wherein each impedance vector encodes the impedances from six or more electrodes, the electrodes being situated on two or more electrode-bearing leads, each lead bearing at least eight electrodes.

6. The implantable stimulator of claim 2 wherein the memory further stores stimulation parameters, each stimulation parameter:
   a. corresponding to an impedance vector, and
   b. defining the electrical stimulation to be delivered by the stimulation generator.

7. The implantable stimulator of claim 1 in combination with an input device:
   a. in communication with the implantable stimulator, and
   b. configured to accept a stimulation parameter which defines the electrical stimulation delivered by the stimulation generator in response to:
      (1) the orientation output signal from the orientation sensor, and
      (2) the impedance of the electrode.

8. The implantable stimulator of claim 7 wherein the input device is in wireless communication with the implantable stimulator.

9. The implantable stimulator of claim 1 further including:
   a. an input device configured to accept a stimulation parameter, wherein the stimulation parameter defines the electrical stimulation delivered by the stimulation generator;
   b. a memory storing an association between the stimulation parameter and:
      (1) the impedance of the electrode at the time of acceptance of the stimulation parameter, and
      (2) the orientation output signal at the time of acceptance of the stimulation parameter;
   wherein the controller is further configured to adjust the electrical stimulation delivered by the stimulation generator to the electrical stimulation defined by the stimulation parameter if:
      i. the impedance of the electrode is at least approximately equal to the impedance of the electrode at the time of acceptance of the stimulation parameter, and
      ii. the orientation output signal is at least approximately equal to the orientation output signal at the time of acceptance of the stimulation parameter.

10. The implantable stimulator of claim 9:
    a. further including an implant housing at least partially surrounding:
       (1) the stimulation generator,
       (2) the lead impedance sensor,
       (3) the orientation sensor, and
       (4) an implant transceiver configured to wirelessly receive communications from the input device;
    b. wherein the input device is separate and spaced from the implant housing.

11. A method for delivering electrical stimulation from an implantable stimulator having a stimulation generator, a lead impedance sensor, an orientation sensor, and a controller, the method including the steps of:
    a. delivering electrical stimulation from the stimulation generator to an electrode of an electrode-bearing lead;
    b. determining the impedance of the electrode of the electrode-bearing lead via the lead impedance sensor;
    c. obtaining an orientation output signal from the orientation sensor, the orientation output signal being indicative of the orientation of the orientation sensor;
    d. adjusting the electrical stimulation delivered by the stimulation generator via the controller, the electrical stimulation being adjusted in dependence on:
       (1) the orientation output signal from the orientation sensor, and
       (2) the impedance of the electrode, wherein the impedance is within a normal operating impedance range representative of unimpaired operation of the electrode-bearing lead.

12. The method of claim 11 wherein the step of adjusting the electrical stimulation delivered by the stimulation generator includes:
    a. comparing:
       (1) the orientation output signal from the orientation sensor, and
       (2) the impedance of the electrode,
       to stored impedance vectors, each impedance vector having a stimulation parameter associated therewith, wherein each stimulation parameter defines the electrical stimulation to be delivered by the stimulation generator;
    b. adjusting the electrical stimulation delivered by the stimulation generator in accordance with the stimulation parameter of the impedance vector most closely corresponding to:
       (1) the orientation output signal from the orientation sensor, and
       (2) the impedance of the electrode.

13. The method of claim 11 further including the step of storing impedance vectors in a memory, each impedance vector encoding:
    a. the orientation output signal from the orientation sensor, and
    b. the impedance of the electrode at or near the time of the orientation output signal.

14. The method of claim 13 further including the step of storing stimulation parameters in the memory, each stimulation parameter:
    a. corresponding to one of the impedance vectors, and
    b. defining the electrical stimulation to be delivered by the stimulation generator.

15. The method of claim 13 further including the step of obtaining a stimulation parameter from a user input device, wherein the stimulation parameter defines the electrical stimulation delivered by the stimulation generator in response to:
    a. the orientation output signal from the orientation sensor, and
    b. the impedance of the electrode.

16. The method of claim 11 further including the steps of:
    a. obtaining a stimulation parameter, wherein the stimulation parameter defines the electrical stimulation delivered by the stimulation generator;
    b. defining an association between the stimulation parameter and:

(1) the impedance of the electrode at the time the stimulation parameter was obtained, and
(2) the orientation output signal at the time the stimulation parameter was obtained;
c. subsequently adjusting the stimulation generator to deliver electrical stimulation corresponding to the stimulation parameter if:
(1) the impedance of the electrode is at least approximately equal to the impedance of the electrode at the time the stimulation parameter was obtained, and
(2) the orientation output signal is at least approximately equal to the orientation output signal at the time the stimulation parameter was obtained.

17. An implantable stimulator including:
a. a lead bearing an electrode, the lead being in an unimpaired state wherein it lacks shorts or breaks;
b. a lead impedance sensor measuring the impedance of the electrode;
c. an orientation sensor measuring the orientation of the implantable stimulator;
d. a stimulation generator:
(1) connected in communication with the electrode, and
(2) generating electrical stimulation signals varying in dependence on:
(i) the measured orientation of the implantable stimulator, and
(ii) the measured impedance of the electrode.

18. The implantable generator of claim 17:
a. further including a memory storing data relating:
(1) implantable stimulator orientations,
(2) electrode impedances, and
(3) electrical stimulation signals;
b. wherein the stimulation generator generates electrical stimulation signals from:
(1) the measured orientation of the implantable stimulator, and
(2) the measured impedance of the electrode,
in accordance with the stored data.

19. The implantable generator of claim 17 in combination with an input device separate from the implantable stimulator, the input device being configured to collect programmer input of data relating:
a. implantable stimulator orientations,
b. electrode impedances, and
c. electrical stimulation signals.

20. The implantable generator of claim 17 wherein:
a. the implantable stimulator includes one or more leads wherein each lead bears one or more electrodes;
b. the stimulation generator generates electrical stimulation signals dependent on:
(1) the measured orientation of the implantable stimulator, and
(2) the measured impedances of three or more of the electrodes.

21. The implantable stimulator of claim 1 wherein the lead impedance sensor is configured to determine the impedance of the electrode of the electrode-bearing lead with respect to at least one of:
a. another electrode on the electrode-bearing lead, and
b. another electrode on another electrode-bearing lead.

22. The method of claim 11:
a. further including the step of determining the impedance of the electrode of the electrode-bearing lead with respect to one or more of:
(1) another electrode on the electrode-bearing lead, and
(2) another electrode on another electrode-bearing lead;
b. wherein the electrical stimulation is:
(1) delivered to more than one of the electrodes, and
(2) adjusted in dependence on more than one of the electrode impedances.

23. The implantable stimulator of claim 17 wherein
a. the lead impedance sensor measures the impedance of the electrode of the electrode-bearing lead with respect to at least one of:
(1) another electrode on the lead, and
(2) another electrode on another lead; and
b. the stimulation generator generates electrical stimulation signals dependent on two or more measured impedances.

* * * * *